United States Patent
Robertson

(10) Patent No.: US 8,280,496 B2
(45) Date of Patent: Oct. 2, 2012

(54) EXTENDED SPECTRAL SENSITIVITY ENDOSCOPE SYSTEM AND METHOD OF USING THE SAME

(75) Inventor: David W. Robertson, Framingham, MA (US)

(73) Assignee: Boston Scientific SCIMED, Inc., Maple Grove, MN (US)

( * ) Notice: Subject to any disclaimer, the term of this patent is extended or adjusted under 35 U.S.C. 154(b) by 865 days.

(21) Appl. No.: 12/332,825

(22) Filed: Dec. 11, 2008

(65) Prior Publication Data

US 2009/0156900 A1 Jun. 18, 2009

Related U.S. Application Data

(60) Provisional application No. 61/013,469, filed on Dec. 13, 2007.

(51) Int. Cl.
*A61B 6/00* (2006.01)
*A61B 5/00* (2006.01)
(52) U.S. Cl. ......... 600/477; 600/342; 600/475; 600/478
(58) Field of Classification Search .................. None
See application file for complete search history.

(56) References Cited

U.S. PATENT DOCUMENTS

| 4,974,076 | A | 11/1990 | Nakamura et al. |
| 5,575,753 | A | 11/1996 | Yabe et al. |
| 5,647,368 | A | 7/1997 | Zeng et al. |
| 5,876,326 | A | 3/1999 | Takamura et al. |
| 6,095,971 | A | 8/2000 | Takahashi |
| 6,296,608 | B1 | 10/2001 | Daniels et al. |
| 6,398,778 | B1 | 6/2002 | Gu et al. |
| 6,443,888 | B1 | 9/2002 | Ogura et al. |
| 6,482,150 | B2 | 11/2002 | Utsui |
| 6,520,908 | B1 | 2/2003 | Ikeda et al. |
| 6,569,087 | B2 | 5/2003 | Naito et al. |
| 6,652,452 | B1 * | 11/2003 | Seifert et al. .................. 600/140 |

(Continued)

FOREIGN PATENT DOCUMENTS

EP 1 526 355 A1 4/2005
(Continued)

OTHER PUBLICATIONS

Communication Relating to the Results of the Partial International Search for PCT/US08/86550, mailed on Apr. 9, 2009; 2 pages.

(Continued)

*Primary Examiner* — Tse Chen
*Assistant Examiner* — Angela M Hoffa
(74) *Attorney, Agent, or Firm* — Finnegan, Henderson, Farabow, Garrett & Dunner, L.L.P.

(57) ABSTRACT

A method according to an embodiment of the invention includes inserting an endoscope at least partially into a body lumen. At least a portion of the body lumen is illuminated at a first wavelength. The portion of the body lumen is illuminated at a second wavelength different than the first wavelength. A characteristic of an area of interest when the portion of the body lumen is illuminated at the first wavelength is compared with the characteristic of the area of interest when the portion of the body lumen is illuminated at the second wavelength. A medical device or treatment parameter is selected to treat the area of interest based on the comparing. In some embodiments, the body lumen is a ureter. In such an embodiment, a composition of a kidney stone within the ureter can be identified.

30 Claims, 9 Drawing Sheets

U.S. PATENT DOCUMENTS

| | | |
|---|---|---|
| 6,873,444 B1 | 3/2005 | Guletsky et al. |
| 6,960,161 B2 | 11/2005 | Amling et al. |
| 7,033,315 B2 | 4/2006 | Smith |
| 7,179,222 B2 | 2/2007 | Imaizumi et al. |
| 7,383,077 B2 * | 6/2008 | Zeng .................. 600/473 |
| 7,907,991 B2 * | 3/2011 | Knapp ................ 600/433 |
| 2004/0148141 A1 | 7/2004 | Tsujita et al. |
| 2004/0225222 A1 | 11/2004 | Zeng et al. |
| 2005/0038322 A1 | 2/2005 | Banik |
| 2005/0080318 A1 | 4/2005 | Squicciarini |
| 2006/0009680 A1 | 1/2006 | Dhindsa |
| 2006/0116552 A1 | 6/2006 | Noguchi et al. |
| 2007/0276259 A1 | 11/2007 | Okawa et al. |
| 2008/0194972 A1 * | 8/2008 | Gono .................. 600/476 |
| 2008/0221457 A1 * | 9/2008 | Zeng et al. ............ 600/477 |
| 2008/0226029 A1 * | 9/2008 | Weir et al. .............. 378/65 |
| 2009/0203991 A1 * | 8/2009 | Papaioannou et al. ........ 600/421 |
| 2009/0259150 A1 * | 10/2009 | Ostrovsky et al. .......... 601/2 |
| 2009/0299187 A1 * | 12/2009 | Bailey et al. ............ 600/449 |
| 2010/0198009 A1 | 8/2010 | Farr et al. |
| 2011/0074943 A1 * | 3/2011 | Modell et al. ............ 348/77 |

FOREIGN PATENT DOCUMENTS

| | | |
|---|---|---|
| WO | WO 02/36015 A1 | 5/2002 |
| WO | WO 2006/076810 A1 | 7/2006 |

OTHER PUBLICATIONS

International Search Report and Written Opinion for PCT/US2008/086550, mailed on Jul. 21, 2009; 18 pages.

* cited by examiner

EXTENDED SPECTRAL SENSITIVITY ENDOSCOPE SYSTEM AND METHOD OF USING THE SAME

CROSS-REFERENCE TO RELATED APPLICATIONS

This application claims priority to U.S. Provisional Patent Application Ser. No. 61/013,469, entitled "Extended Spectral Sensitivity Endoscope System and Method of Using the Same," filed Dec. 13, 2007, the disclosure of which is hereby incorporated by reference in its entirety.

BACKGROUND

The invention relates generally to medical devices and more particularly to endoscope devices and methods for using such devices.

A variety of known types of endoscopes that can be used for various medical procedures, such as procedures within a urogenital or gastrointestinal system and vascular lumens. Some known endoscopes include optical fibers for providing light and/or imaging capabilities. Some known endoscopes include filter devices or systems to control and/or change the type of light being emitted into the treatment site. For example, some electronic endoscopes can filter at different wavelengths to select between visible light, ultraviolet light, and infrared light. Some known endoscopes include various working channels to allow for the insertion of various medical tools through the working channels and into a body lumen. For example, biopsy tools, forceps, or other devices can be used to treat a tissue within a body lumen. Irrigation and/or suction devices can also be disposable within a channel of an endoscope, or such devices can be incorporated within an endoscope.

Improvements in diagnostic techniques using an endoscope are needed to identify an area (e.g., tissue) within a body lumen that needs medical treatment. With identification, a treatment method and/or type of treatment device can be readily selected so that the treatment more closely matches the treatment area.

Thus, a need exists for an endoscope system that can identify a tissue site to be treated, such that a proper medical device(s) and/or treatment parameters can be selected and used to treat the tissue site.

SUMMARY OF THE INVENTION

A method according to an embodiment of the invention includes inserting an endoscope at least partially into a body lumen. At least a portion of the body lumen is illuminated at a first wavelength. The portion of the body lumen is illuminated at a second wavelength different than the first wavelength. A characteristic of an area of interest when the portion of the body lumen is illuminated at the first wavelength is compared with the characteristic of the area of interest when the portion of the body lumen is illuminated at the second wavelength. A medical device(s) and/or treatment parameter(s) is selected to treat the area of interest based on the comparing. In some embodiments, the body lumen is a ureter. In such an embodiment, a composition of a kidney stone within the ureter can be identified.

DETAILED DESCRIPTION

Figure 1:
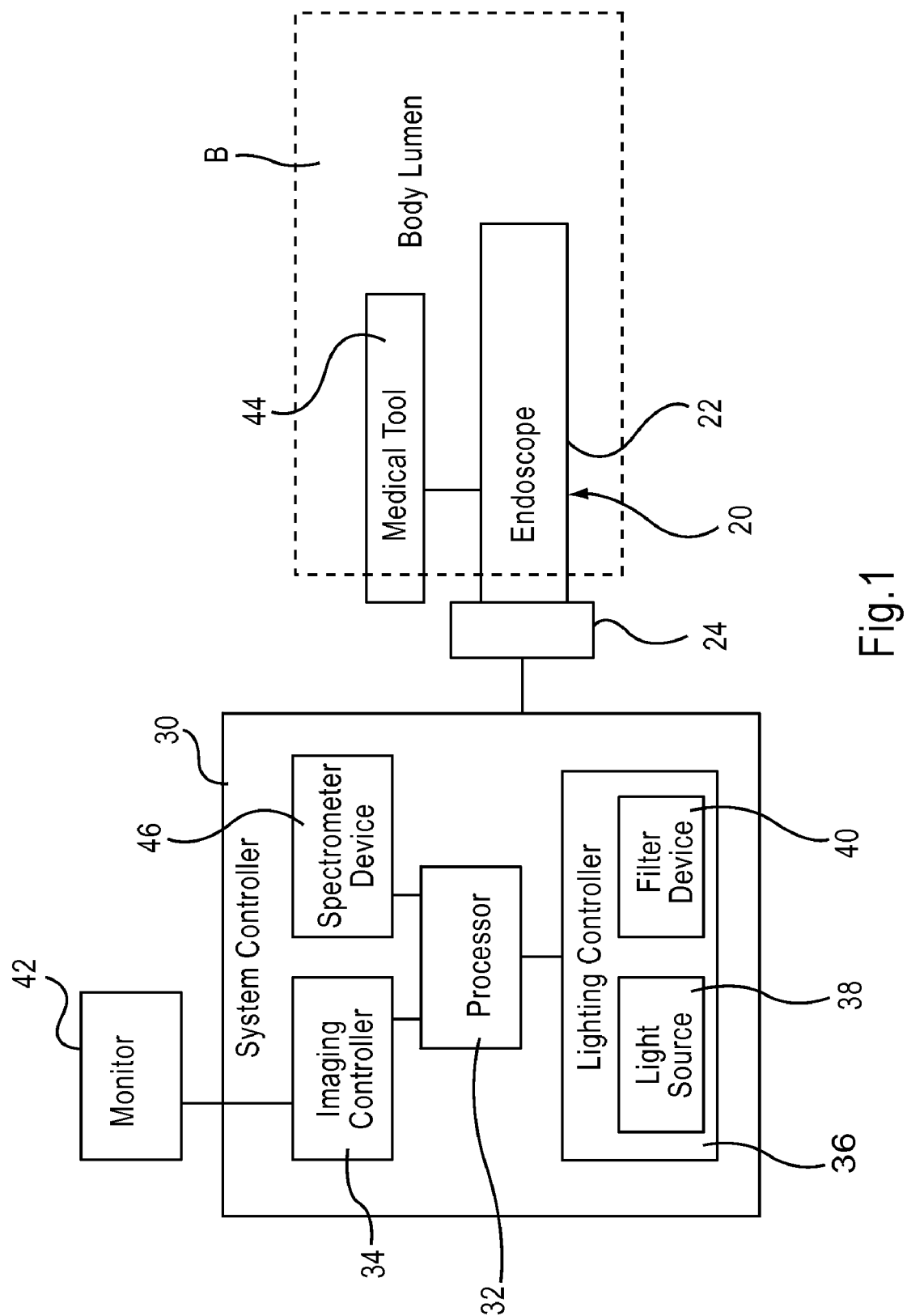
FIG. 1 is a schematic illustration of an endoscope device and system according to an embodiment of the invention.
Figure 2:
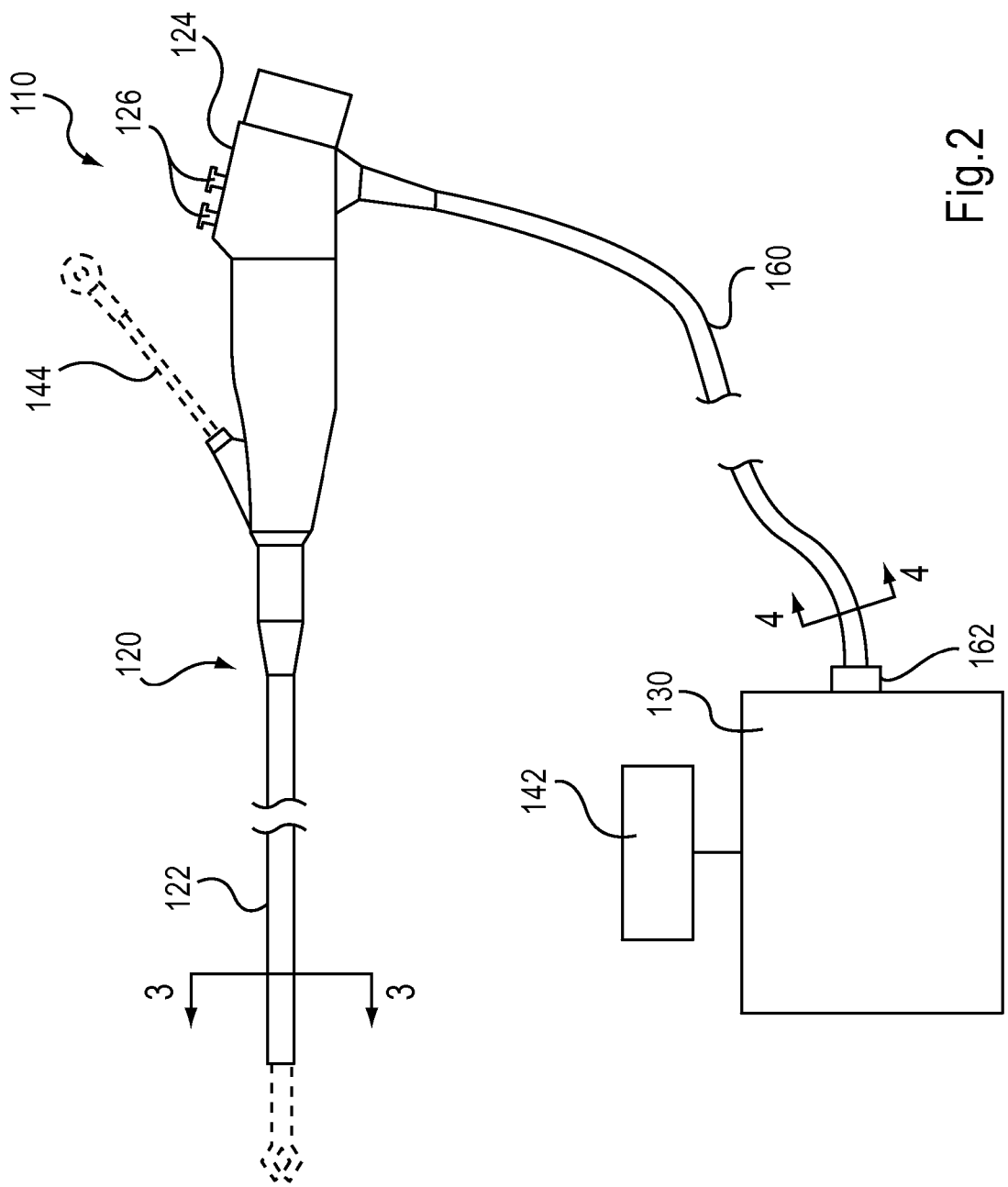
FIG. 2 is a side view of an endoscope system according to an embodiment of the invention.

The devices and methods described herein are generally directed to the use of an endoscope within a body lumen of a patient. For example, the devices and methods are suitable for use within a gastrointestinal lumen, or a ureter. An endoscope system as described herein can be used to illuminate the body lumen at various different wavelengths of light, such as, for example, visible light, infrared light, and/or ultraviolet light. The endoscope can include an image sensor, such as, for example, a charge-coupled device (CCD) or a complementary metal-oxide-semiconductor (CMOS), that can be used to take images of the body lumen when the body lumen is illuminated at the different wavelengths of light. Comparisons of the images can identify differences in shape, composition, luminescence, etc. of an identified area of interest within the body lumen.

In some embodiments, visual comparison of the area of interest can be made, for example, by viewing the area of interest through an eyepiece coupled to, or incorporated within, the endoscope when the body lumen is illuminated at the various wavelengths of light. In some embodiments, a processor can analyze images of the body lumen when illuminated at the different wavelengths of light. For example, the images can be converted to electronic signals and various parameters can be compared. In another example, the processor can analyze the images so that various characteristics of the area of interest can be distinguished.

In one embodiment, a method includes inserting an endoscope at least partially into a body lumen. At least a portion of the body lumen is illuminated at a first wavelength. The portion of the body lumen is illuminated at a second wavelength different than the first wavelength. A characteristic of an area of interest when the portion of the body lumen is illuminated at the first wavelength is compared with the characteristic of the area of interest when the portion of the body lumen is illuminated at the second wavelength. A medical device(s) and/or treatment parameter(s) is selected to treat the area of interest based on the comparing.

In another embodiment, a method includes illuminating at least a portion of a ureter at a first wavelength. The portion of the ureter is illuminated at a second wavelength different than the first wavelength. Based on the illuminating at the first wavelength and the illuminating at the second wavelength, a composition of a kidney stone is identified within the ureter. In another embodiment, a method includes inserting an endoscope at least partially into a ureter. At least a portion of the ureter is illuminated at a first wavelength and illuminated at a second wavelength different than the first wavelength. An image of the ureter when illuminated at the first wavelength is compared to an image of the ureter when illuminated at the second wavelength. A medical device(s) and/or treatment parameter(s) is then selected to treat an area of interest within the ureter based on the comparing.

It is noted that, as used in this written description and the appended claims, the singular forms "a," "an" and "the" include plural referents unless the context clearly dictates otherwise. Thus, for example, the term "a wavelength" is intended to mean a single wavelength or a combination of wavelengths. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body. Thus, for example, the endoscope end inserted inside a patient's body would be the distal end of the endoscope, while the endoscope end outside a patient's body would be the proximal end of the endoscope.

FIG. 1 is a schematic representation of an endoscope system according to an embodiment of the invention. An endoscope 20 includes an elongate portion 22 that can be inserted at least partially into a body lumen B, and a handle portion 24 outside the body lumen B. The endoscope 20 also includes one or more lumens extending through the elongate portion and/or handle portion. The elongate portion can be flexible, or can include a portion that is flexible, to allow the elongate portion to be maneuvered within a body lumen. The endoscope 20 can be inserted into a variety of different body lumens such as, for example, a ureter, a gastrointestinal lumen, an esophagus, a vascular lumen, etc. The handle portion can include one or more control mechanisms that can be used to control and maneuver the elongate portion of the endoscope 20 through the body lumen.

As stated above, the endoscope 20 can define one or more lumens. In some embodiments, the endoscope 20 includes a single lumen that can receive therethrough various components. For example, optical fibers or electrical wires can pass through a lumen of the endoscope 20 to provide illumination and/or imaging capabilities at a distal end portion of the endoscope 20. The endoscope 20 can also be configured to receive various medical devices or tools 44 through one or more lumens of the endoscope, such as, for example, irrigation and/or suction devices, forceps, drills, snares, needles, etc. An example of such an endoscope with multiple lumens is described in U.S. Pat. No. 6,296,608 to Daniels et, al., the disclosure of which is incorporated herein by reference in its entirety. In some embodiments, a fluid channel is defined by the endoscope 20 and coupled at a proximal end to a fluid source. The fluid channel can be used to irrigate an interior of a body lumen. In some embodiments, an eyepiece can be coupled to a proximal end portion of the endoscope 20, for example, adjacent the handle 24, and coupled to an optical fiber that can be disposed within a lumen of the endoscope 20. Such an embodiment allows a physician to view the interior of a body lumen through the eyepiece.

A system controller 30 can be coupled to the endoscope 20 and configured to control various elements of the endoscope 20 as described in more detail below. The system controller 30 can include a processor 32, an imaging controller 34, a lighting controller 36, and/or a spectrometer 46. In alternative embodiments, each of these devices can be provided as separate components, separate from the system controller 30. The lighting controller 36 can include a light source 38 and a filter device 40. The light source 38 can be configured to provide light at various different wavelengths. The filter device 40 includes a filter member (not shown in FIG. 1) and a filter controller (not shown in FIG. 1). The imaging controller 34 includes an imaging device (not shown in FIG. 1) and a processor (not shown in FIG. 1), and can be coupled to a monitor 42. The endoscope 20 can include optical fibers configured to transmit light back to the spectrometer device 46 for a spectral analysis of the interior of the body lumen.

The endoscope 20 can also include an image sensor or imaging device (not shown in FIG. 1) coupled to a distal end portion of the elongate portion 22 of the endoscope 20. The image sensor can be, for example, a solid state imaging detector, such as a charge-coupled device (CCD) or a complementary metal-oxide-semiconductor (CMOS). The image sensor can be coupled to the imaging controller 34 via electrical wires that pass through a lumen of the endoscope 20. Thus, images of a body lumen can be captured by the image sensor and processed by the imaging controller 34. The images can also be displayed on the monitor 42.

In some embodiments, the image sensor includes an optical filter. The optical filter can filter optical energy captured by pixels of the image sensor. For example, the optical filter can be disposed on or in front of the image sensor (i.e., between the image sensor and the distal end of the endoscope 20) so that the optical filter filters optical energy before being captured by the image sensor. This filter can be associated with different wavelengths or bands of wavelengths for different pixels. In alternative embodiments, the filter device 40 may not be included and an unfiltered image can be captured via the image sensor for processing.

The endoscope 20 can also include illumination fibers (not shown in FIG. 1) that can be coupled to the lighting controller 36. The illumination fibers can be used to transfer light from the light source 38, through the endoscope 20, and into the body lumen B. Illumination fibers can also be used to transfer light to the spectrometer 46. The illumination fibers can be formed, for example, with a quartz glass component or other suitable glass or polymer material capable of transmitting and receiving various wavelengths of light. The illumination fibers can be a single fiber or a bundle of multiple fibers. The light source 38 can be configured to transport light at a variety of different wavelengths. For example, the light source 38 can transport light at various wavelengths associated with visible light, infrared light and/or ultraviolet light. The filter device 40 can be controlled by the lighting controller 36, and used to selectively control the wavelength(s) of light that can be transmitted to the illumination fibers. For example, the filter device 40 can selectively block wavelengths of light in the visible light range and the ultraviolet light range, and allow only a band of wavelengths of light in the infrared range to pass through the filter device 40. The filter device 40 and light source 38 can also be configured to provide illumination at more than one band of wavelengths of light at a time. For example, illumination can be provided with both infrared and visible light. In some embodiments, illumination can be provided with only a portion of a band of wavelengths. For example, a band of wavelengths associated with visible light can be provided that includes only green. In some embodiments, a band of wavelengths associated with infrared light can be provided that includes, for example, just near-infrared.

The processor 32 of the systems controller 30 can be operatively coupled to the lighting controller 36 and the imaging controller 34. The processor 32 (e.g., central processing unit (CPU)) includes a memory component, and can store and process images or other data received from the endoscope 20. The processor 32 can analyze images, and calculate and analyze various parameters and/or characteristics associated with an image or other data provided by the endoscope. The processor 32 can be operatively coupled to the various components of the system controller 30. As stated above, in alternative embodiments, the lighting controller 36, the imaging controller 34 and/or spectrometer device 46 are separate devices and can be coupled to the endoscope 20 using a separate connector or connectors. In such an embodiment, the imaging controller 34, lighting controller 36, and spectrometer device 46 can optionally be coupled to each other and/or a system controller 30.

The endoscope 20 can be used to illuminate and image a body lumen B, and can also be used to diagnose an area of interest (e.g., a tissue, a tumor, a kidney stone, a polyp, etc.) within the body lumen B. The endoscope 20 can be inserted at least partially into a body lumen B, such as a ureter, and the lighting controller 36 and illumination fibers collectively can be used to illuminate the ureter or a portion of the ureter at various different wavelengths. For example, the ureter can be illuminated at a first band of wavelengths, such as at a band of wavelengths associated with visible light (e.g., 380 nm to 780 nm). The ureter can be observed while being illuminated via an eyepiece as described above, or the ureter can be imaged using the imaging controller 34 and imaging device (e.g., CCD or CMOS). In embodiments where the endoscope 20 is coupled to a spectrometer 46, the light intensity can also be measured. For example, the portion of the image associated with the area of interest can be measured by the spectrometer 46.

The ureter can then be illuminated at a different band of wavelengths, such as a band of wavelengths associated with infrared light or a band of wavelengths associated with ultraviolet light. For example, the filter device 40 can be used to control the type of wavelengths of light that is allowed to be transmitted via the illumination fibers or sensing fibers to the spectrometer. In some embodiments, the ureter can be illuminated at both a band of wavelengths of visible light and a band of wavelengths of, for example, infrared light. In such an embodiment, an image can then be taken of the illuminated portion of the ureter. The image can be filtered and analyzed by the system processor and one or more areas of interest can be identified. For example, the image can be displayed on the monitor 42, and areas that are more intense in the visible image can indicate a specific composition of a tissue, such as composition of a kidney stone. A spectral analysis can also be performed.

In some embodiments, the ureter can be illuminated at a band of wavelengths for visible light and then imaged. Then the ureter can be illuminated at a second band of wavelengths such as, for example, a band of wavelengths for infrared light, and then imaged. A comparison of the two images can indicate an area of interest, such as a kidney stone. For example, certain compositions of a kidney stone can display as a certain intensity, reflectivity or brightness or florescence as a function of illumination wavelength.

Thus, various characteristics of an area of interest can be analyzed based on a comparison of the captured images or on spectral data collected when the body lumen is illuminated at different wavelengths of light. Such characteristics can include, for example, a size or shape of the area of interest and/or color intensity, reflectivity, florescence and/or brightness as a function of wavelength of the area of interest. In another example, a photometric measure of the density of luminous intensity in a given direction (e.g., luminance) of the area of interest can be determined. Such a characteristic can be measured, for example, in candela per square meter ($cd/m^2$).

The analyses of the captured images and/or the spectral data can be used to assist in determining a course of treatment (e.g., medical device) for the area of interest. Imaging of the area of interest can continue during application of the chosen medical device or treatment parameters, (continuously or during short breaks in application). Images can be compared for changes in color intensity, light reflectivity, brightness, and/or florescence, and/or size and/or shape of the area of interest. Recommendations can be made for changes in the medical device or treatment parameters for the area of interest to optimize the application. Such recommendations can be based on, for example, changes or rates of change to a particular parameter. The processor of the endoscope system can provide, for example, closed-loop feedback control of treatment parameters, such as laser lithotripsy pulse rate and energy per pulse, in conjunction with the medical device performing the treatment.

In some embodiments, the illumination source of the band of wavelengths can be provided by the treatment device (e.g., in the case of laser lithotripsy) or other high energy laser light. Emissions of vapor bubbles, vapors, by-products of chemical decomposition, combustion, or plasmas, (electromagnetic or chemical sensed spectrographically) can also be used in choosing or controlling treatment parameters.

For example, the identification of a composition of a kidney stone can help determine the type of lithotripsy or laser tool to use, and/or treatment parameters, to break-up the kidney stone. There are several different types of kidney stone composition. The most common type of kidney stone (about 70-80% of all stones) is a calcium oxalate stone. This type of stone is most likely to be treated with medications to help prevent calcium stones if they have a propensity to recur. About 6% of calcium stones are composed of calcium phosphate (called brushite).

Uric acid stones are commonly associated in patients with gout or increased levels of uric acid in the urine. Uric acid stones are made of uric acid, which is formed from a breakdown in purine, a nitrogen compound found in protein, and can be dissolved by changing the pH (basic vs. acidic) of the urine with medications. Struvite stones are often called "infection stones," as they are often associated with a urinary tract infection. At times these stones can be extremely large and fill the entire collecting system of the kidney. Cystine stones are formed due to an inherited disorder of amino acid metabolism. This type of stone commonly runs in families and can be very difficult to manage since they have a tendency to recur. Lastly, there are xanthine stones, which are composed of xanthine, a nitrogen compound, and are extremely uncommon and usually occur as a result of a rare genetic disorder.

The specific treatment procedure can depend on the size of the stone or complexity of the situation. Noninvasive procedures are typically preferred over invasive surgeries. For small stones that are lodged in the lower part of a ureter, ureteroscopy or shock wave lithotripsy are common procedures to treat the kidney stone. For larger stones, ureteroscopy, percutaneous nephrolithotomy, and shock wave lithotripsy are all common procedures, depending on location, abnormalities, and other considerations. In some complicated cases, standard open surgical procedures (called nephrolithotomy) may be desired.

For example, if a kidney stone is identified as a calcium oxalate stone, or a uric acid stone, a procedure such as ballistic lithotripsy, electro-hydraulic lithotripsy, or laser lithotripsy, can be performed during ureteroscopy, percutaneous nephrolithotomy, or open surgery for struvite or cystine stones. Furthermore, appropriate treatment parameters may vary for each procedure and each stone type.

Figure 3:
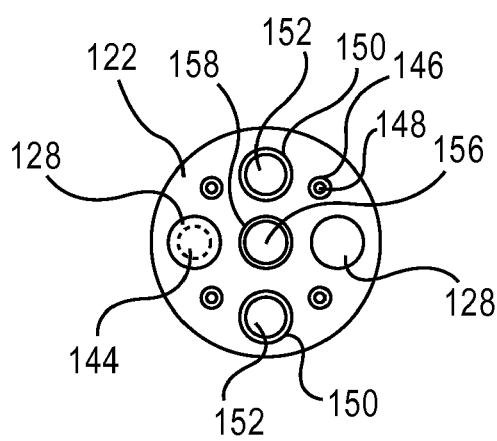
FIG. 3 is a cross-sectional view of the endoscope of FIG. 2 taken along line 3-3 in FIG. 2.
Figure 4:
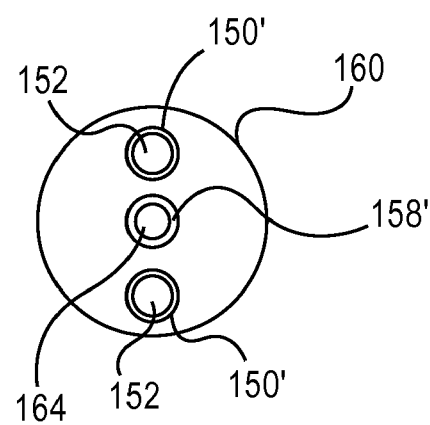
FIG. 4 is a cross-sectional view of the endoscope of FIG. 2 taken along line 4-4 in FIG. 2.

FIGS. 2-8 illustrate an endoscope system 110 according to an embodiment of the invention. The endoscope system 110 includes an endoscope 120 and a system controller 130. The endoscope 120 can be coupled to the system controller 130 with a universal cord 160 coupled to a connector 162. The endoscope 120 includes a flexible elongate portion 122, a handle portion 124, and an image sensor 156 (FIG. 3) disposed at a distal end portion of the flexible elongate portion 122. The image sensor 156 can be an imaging device, such as a CCD or CMOS, as described above. The image sensor 156 can be coupled to the system controller 130 via electrical wires 164 (FIG. 4) that extend through a channel 158 of the flexible elongate portion 122 and handle portion 124, and through corresponding channel 158' of the universal cord 160. The endoscope 120 also includes multiple illumination fibers 152 that are disposed within two fiber channels 150 of the flexible elongate portion 122 and handle portion 124 and corresponding channels 150' of the universal cord 160, as shown in FIGS. 3 and 4.

As shown in FIG. 3, the endoscope 120 defines two working channels 128 that extend through the flexible elongate portion 122 and a portion of the handle portion 124. The working channels 128 can receive various components therethrough. For example, a medical tool 144 is shown disposed in one of the working channels 128. The flexible elongate portion 122 also includes four control channels 146 (FIG. 3), each having a control wire 148 disposed therein. The control wires 148 are coupled to control mechanisms 126 on the handle 124 and are used to maneuver the flexible elongate portion 122 through a body lumen.

The system controller 130 includes a processor 132, an imaging controller 134, and a lighting controller 136. As stated above, in other embodiments, the system controller can include some of these components, and in other embodiments, some or all of these components are included in an endoscope system, but as separate components operatively coupled to the endoscope. The processor 132 can be operatively coupled to the imaging controller 134 and the lighting controller 136. The system controller 130 can include a control panel (not shown) with master controls that can used to operate the various components of the endoscope system 110.

Figure 6:
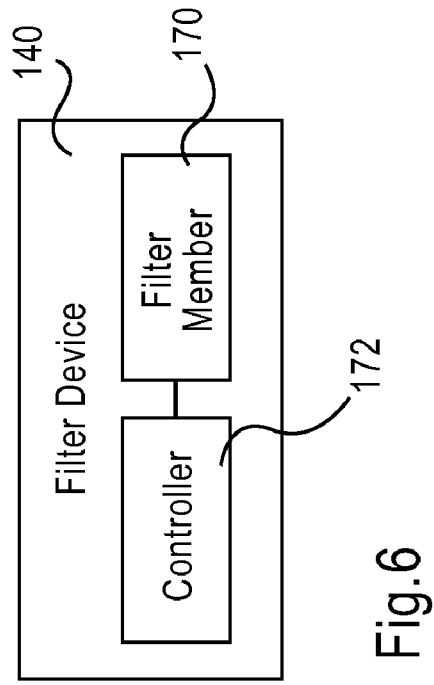
FIG. 6 is a schematic representation of the filter device of FIG. 5.
Figure 5:
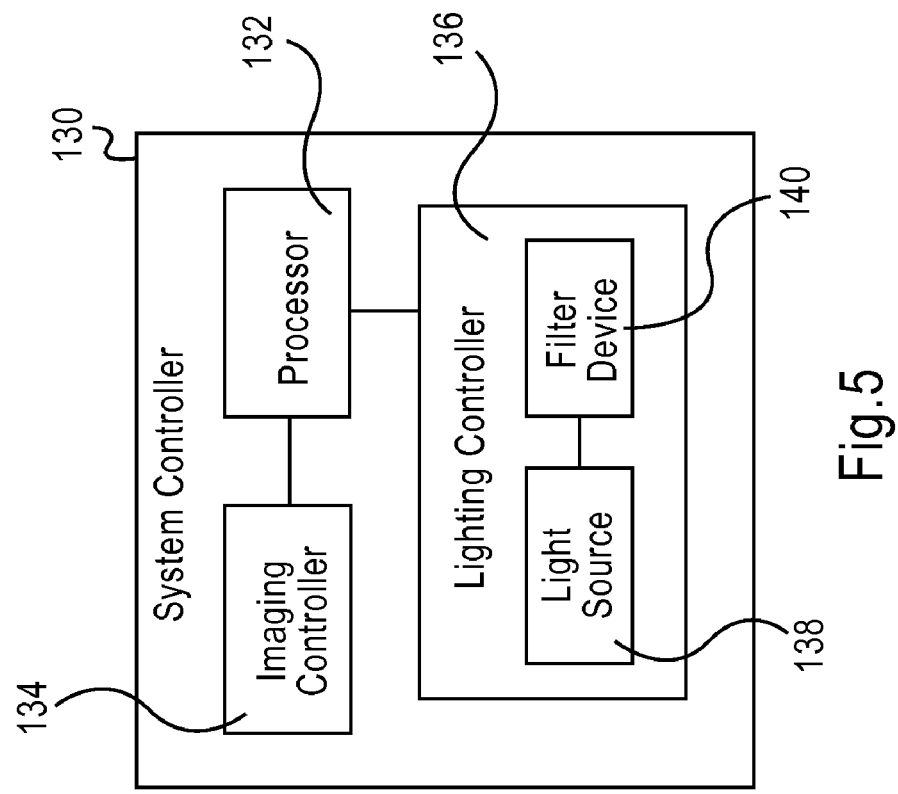
FIG. 5 is a schematic representation of the system controller of FIG. 2.

As shown in FIGS. 5 and 6, the lighting controller 136 includes a light source 138 operatively coupled to a filter device 140. The filter device 140 includes a filter member 170 and a controller 172. The illumination fibers 152 are coupled to the light source 138 via the universal cord 160. The light source 138 can be configured to provide light to the illumination fibers 152 at various different wavelengths, such as, for example, bands of visible light, ultraviolet light and/or infrared light. As described previously, the filter device 140 can be used to control the type of light being conveyed from the light source 138 to the illumination fibers 152. For example, the controller 172 can be used to operatively control the filter member 170 to selectively control the wavelength of light to be transferred from the light source 138 to the illumination fibers 152.

Figure 7:
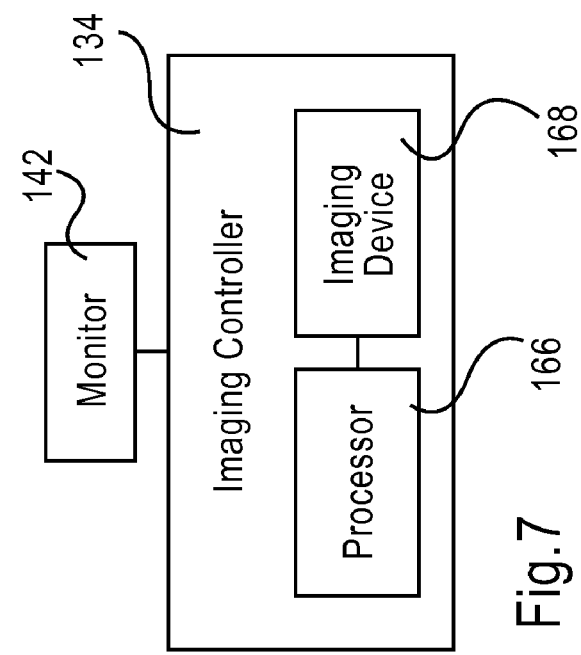
FIG. 7 is schematic representation of the lighting controller of FIG. 6.

As shown in FIG. 7, the imaging controller 134 includes a processor 166 and an imaging device 168 that is operatively coupled to the image sensor 156 via the wires 164. The imaging controller 134 and image sensor 156 can be used to image an interior of a body lumen, such as a ureter, when the body lumen is illuminated with the illumination fibers 152. The imaging controller 134 is also coupled to a monitor 142 to allow viewing of image(s) taken of a body lumen. The processor 166 can be used to analyze the image(s) of the body lumen. For example, the processor 166 can compare images taken at different wavelengths of light and/or at different time periods. The processor 166 can analyze various characteristics of an area of interest within the body lumen, such as, for example, differences in shape and/or size of an area of interest as indicated in different images. In another example, the processor 166 can analyze a the brightness, the reflectivity and/or the intensity of an area of interest as a function of wavelengths and as indicated on different images. Thus, various characteristics or parameters of captured or spectral data can be evaluated and the data can be provided to a physician, for example, via the monitor 142, or via reports that can be generated and printed on a printer (not shown) coupled to the system controller 130.

The endoscope system 110 can be used to illuminate and image a portion of a body lumen, such as, for example, a ureter. The flexible elongate portion 122 of the endoscope 120 can be maneuvered through the body lumen with the control mechanisms 126 on the handle 124. Once positioned at a desired location within the body lumen, the body lumen can be illuminated at a selected band of wavelengths of light, such as, for example, a band of wavelengths associated with visible light, with the imaging controller 136 and illumination fibers 152. The body lumen can then be imaged using the image sensor 156 and imaging controller 134 while illuminated at the selected wavelength of light. The filter device 140 can then be operated to change the band of wavelengths of light to illuminate the body lumen at a different band of wavelengths of light, such as, for example, a band of wavelengths associated with infrared light or a band of wavelengths associated with ultraviolet light. The body lumen can again be imaged while being illuminated at the second band of wavelengths of light.

The images taken of the body lumen while illuminated at both the first band of wavelengths of light and the second band of wavelengths of light can then be analyzed with the processor 166. For example, a comparison of the images can identify an area of interest, such as a tumor, a kidney stone or other tissue site within the body lumen. This identification can be based on, for example, one or more differences at the location of the area of interest between the two images. Various characteristics of the area of interest can then be analyzed, such as for example, a difference in color intensity, light reflectivity and/or brightness and/or florescence, and/or size and/or shape of the area of interest as a function of wavelength. The characteristics can help reveal, for example, information regarding the composition of the area of interest. For example, when an ureter is the body lumen being analyzed, a kidney stone can be identified. One or more characteristics of the kidney stone can be analyzed to determine the composition of the kidney stone. This information can help in a determination of the type of medical tool or treatment parameters that should be used to treat or remove the kidney stone. For example, based on the composition of the kidney stone, a type of lithotripsy device or treatment parameters can be selected.

Thus, with information about the area of interest, a proper medical device(s) and/or treatment parameter(s) can be selected to treat the area of interest. The selected medical device can be inserted through a working channel 128 of the endoscope 122 and used to treat the area of interest, without having to remove the endoscope 120. In some cases, it may be desirable to perform a separate medical procedure to treat the area of interest.

Figure 8:
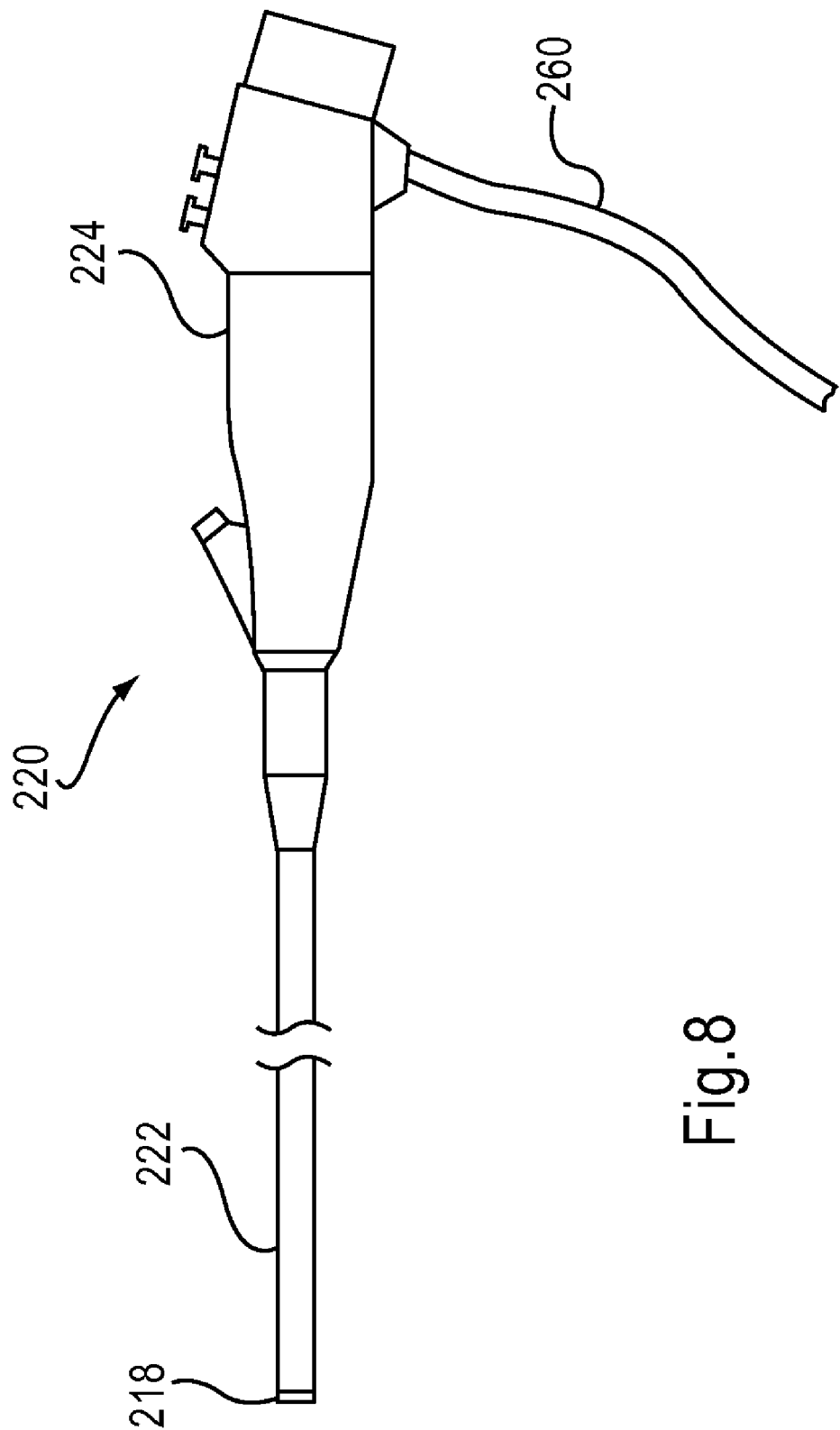
FIG. 8 is a side view of an endoscope according to another embodiment of the invention.

As stated previously, in some embodiments, an endoscope can include an optical filter coupled to or in front of an image sensor (e.g., CCD or CMOS). For example, the filter can be placed over the pixel sensors of the image sensor. Such an embodiment of an endoscope is illustrated in FIG. 8. In this embodiment, an endoscope 220 includes an elongate portion 222, a handle portion 224, an image sensor (not shown) and a filter 218 coupled to a distal end portion of the elongate portion 222 or the image sensor. The filter 218 is shown coupled to the end of the elongate portion 222 for illustration purposes, as the filter 218 can alternatively be disposed within a lumen of the elongate portion 222, flush with an end of the elongate portion 222, incorporated with the image sensor, or coupled to the image sensor.

The endoscope 220 also includes optical fibers (not shown) configured to transport light at various bands of wavelengths as in the previous embodiments. The endoscope 220 can include any of the features as the previous embodiments and be used in the same or similar manner as described above. For example, the endoscope 220 can be operatively coupled to a system controller (not shown) or other devices or source(s) of power, light, etc., via a cord or cable 260. Alternatively, the endoscope 220 can be coupled to multiple different devices, via one or more cords, cables, etc.

The filter 218 is disposed in front of the pixels of the image sensor, and can be configured to filter or pass to on a per-pixel basis selected bands of wavelengths of light, such as for example, bands of wavelengths associated with visible light, bands of wavelengths associated with ultraviolet light, and/or bands of wavelengths associated with infrared light. For example, a filter 218 can be configured to filter or pass to different selected pixels, visible light, ultraviolet light, infrared light, near ultraviolet light, or near infrared light, etc.

The endoscope 220 can be used to illuminate an interior of a body lumen as described above, such as a ureter, with one or more bands of wavelengths of light. An image can be captured of the body lumen while illuminated, and the filter 218 can filter the light to selected pixels. For example, the body lumen can be illuminated with visible light, ultraviolet light and infrared light at the same time. An image can be captured of the body lumen while so illuminated, and the filter 218 can pass selected bands of light to selected pixels, thereby separating the light into separate pixels. From this imaging, multiple images of the body lumen can be produced that include only the pixels associated with a selected type of light. For example, an image can be produced that includes only the pixels associated with visible light, another image can include only the pixels associated with ultraviolet light, and another image can include only the pixels associated with the infrared light. Thus, the body lumen can be imaged while being illuminated with multiple different types of light, and multiple images can be produced associated with the individual types of light. Such images can then be compared and analyzed to identify an area of interest, such as a kidney stone as described previously.

Figure 9:
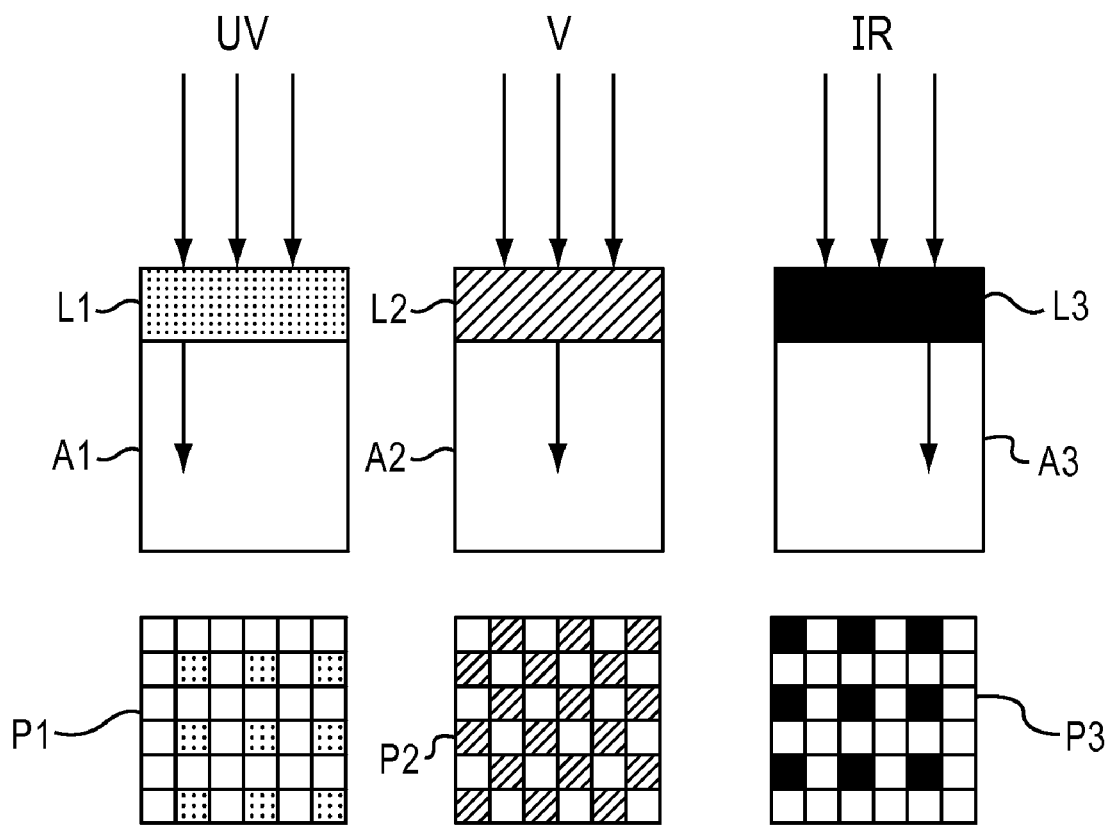
FIG. 9 is a schematic representation of a filter member and image sensor according to an embodiment of the invention.

FIG. 9 is a schematic illustration of the use of a filter 218. As show in FIG. 9, light can be provided at different bands of wavelengths of light, such as, for example, visible light V, infrared light IR, and ultraviolet light UV. Filter layers L1, L2, and L3, represent the filter 218, and the filter or sensor arrays A1, A2, and A3 represent the capturing and passing of selected bands of wavelengths of light to selected pixels. The resulting pixel patterns are illustrated as P1, P2, and P3. In this illustration, 1 out of 4 pixels are associated with ultraviolet light UV, 1 out of 4 pixels are associated with infrared light, and 2 out of 4 pixels are associated with visible light V. A filter can alternatively be configured with a different distribution of the pixels. Thus, an image including the pattern P1 includes only the pixels associated with ultraviolet light UV. An image including the pattern P2 includes only the pixels associated with visible light V, and an image including the pattern P3 includes only the pixels associated with infrared light IR. Additionally, the image sensor may be used without any filters to allow all pixels to record any wavelengths reflected or emitted by the region of interest when illuminated by one or more bands of wavelengths of light.

In alternative embodiments, an endoscope system can include a filter that is a fluid or colloid, or series of fluids or colloids, which are injected into the body lumen through the irrigation channel of the endoscope (or an external catheter). The filter (e.g., fluid or colloid) surrounds or bathes the region of interest to block, enhance, or shift illumination or image wavelengths.

The various components of the endoscope (e.g., 20, 120, 220) described herein can be formed with a variety of different biocompatible plastics and/or metals. For example, the elongate body of the endoscope can be formed with one or more materials such as, titanium, stainless steel, or various polymers. The optical fibers can be formed with various glass or plastic materials suitable for such uses. The optical fibers can also include a cladding formed with a polymer or other plastic material.

Figure 10:
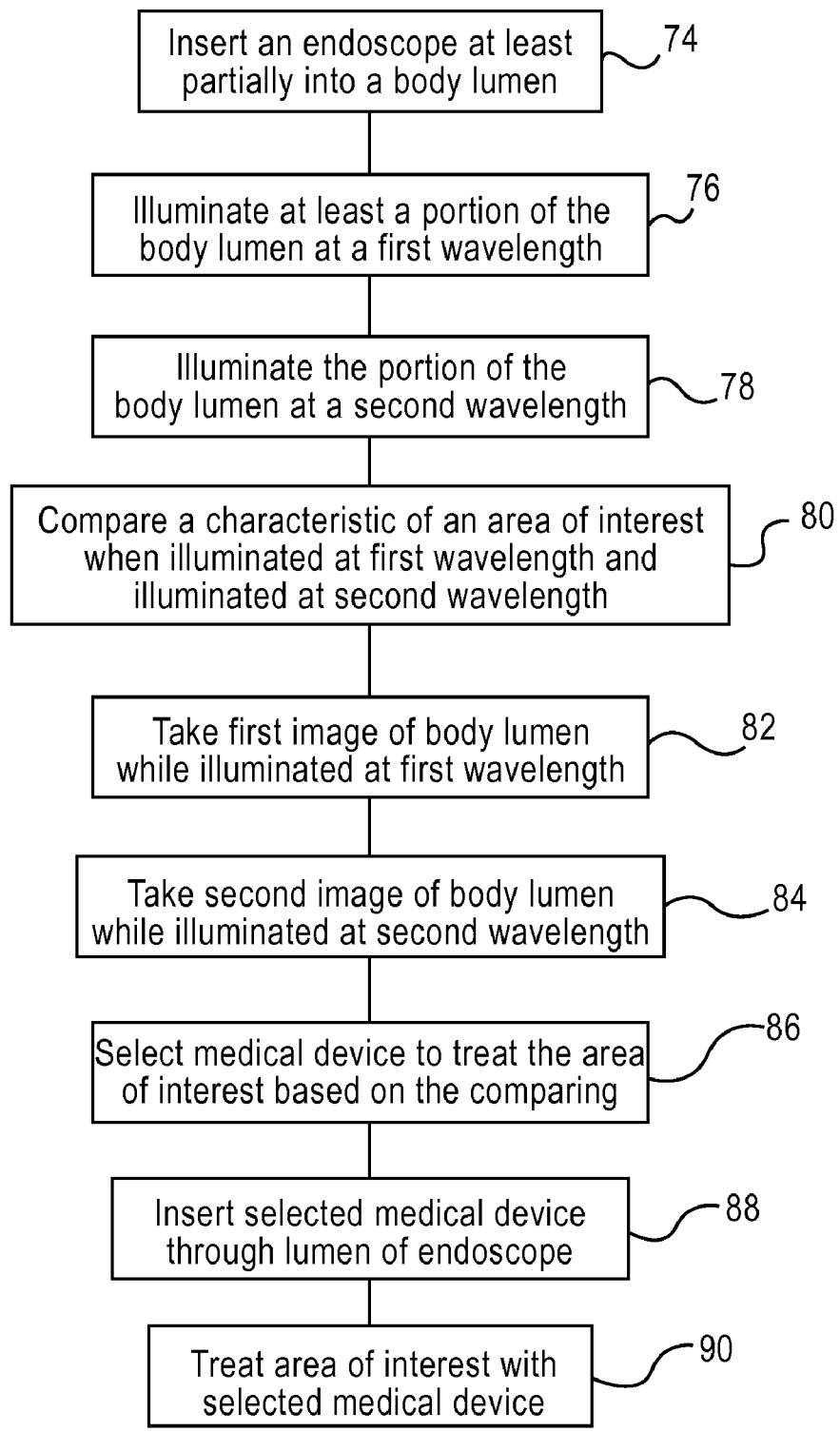
FIG. 10 is a flowchart illustrating a method according to an embodiment of the invention.

FIG. 10 is a flow chart illustrating a method of using an endoscope system according to an embodiment of the invention. At 74, an endoscope is inserted at least partially into a body lumen. The body lumen can be for example, a ureter. At 76, at least a portion of the body lumen is illuminated at a first set of wavelengths. The first set of wavelengths can be, for example, a band of wavelengths associated with visible light, a band of wavelengths associated with infrared light, or a band of wavelengths associated with ultraviolet light. At 78, the portion of the body lumen is illuminated at a second set of wavelengths different than the first set of wavelengths. The second set of wavelengths can include the same bands of wavelengths (e.g., visible light, infrared light, or ultraviolet light) as for the first set of wavelengths. At 80, a characteristic of an area of interest is compared when the portion of the body lumen is illuminated at the first set of wavelengths with the characteristic of the area of interest when the portion of the body lumen is illuminated at the second set of wavelengths. At 82, a first image can optionally be taken during at least a portion of the illuminating of the body lumen at the first wavelength, and at 84 a second image of the portion of the body lumen can optionally be taken during at least a portion of the illuminating of the body lumen at the second wavelength. In such an embodiment, the comparing can be based on a comparison of the first image and the second image. At 86, a medical device(s) and/or treatment parameter(s) is selected to treat the area of interest, based on the comparing at 80. Optionally, the selected medical device can be inserted through a lumen of the endoscope at 88, and used to treat the area of interest at 90.

Figure 11:
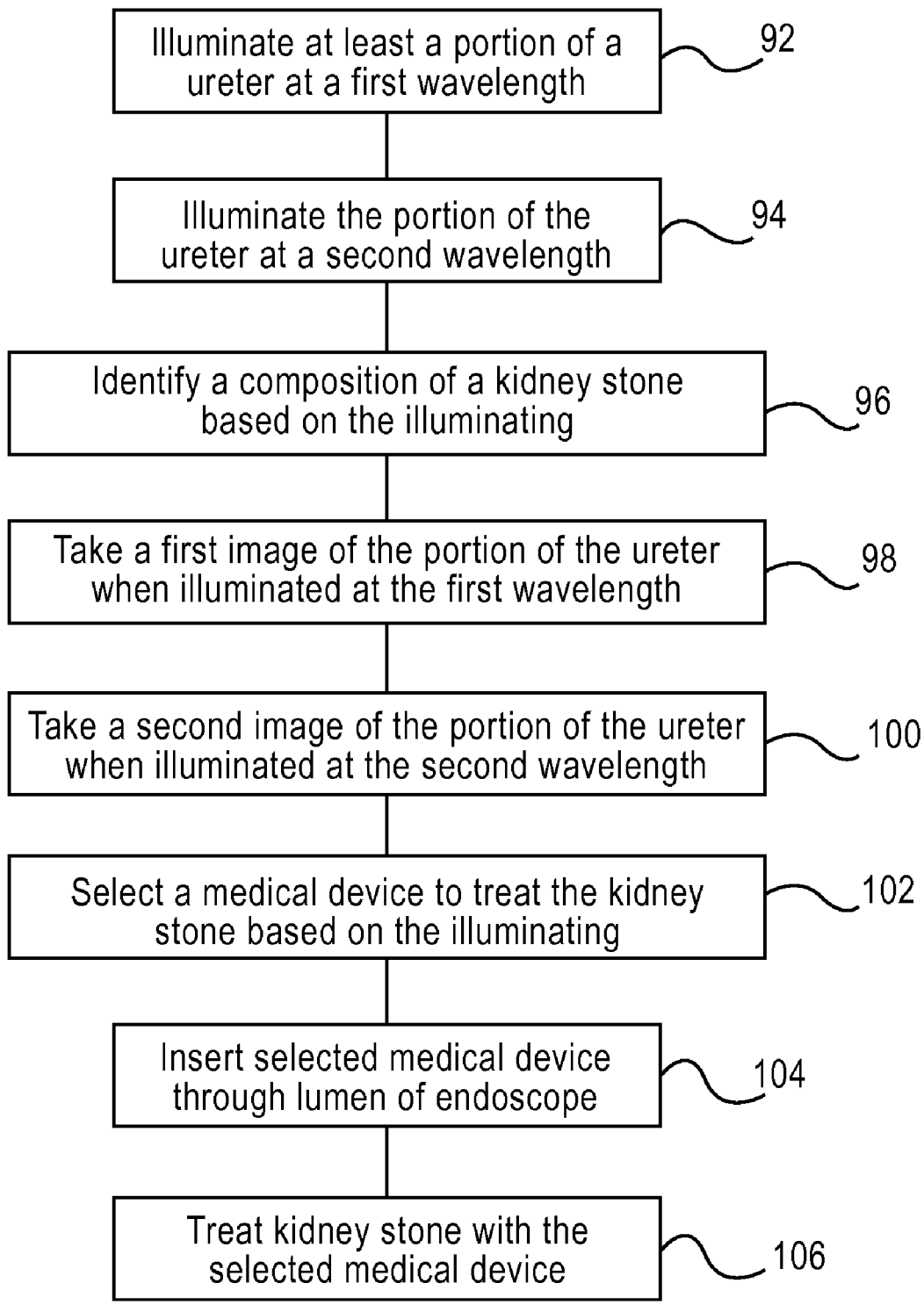
FIG. 11 is a flowchart illustrating a method according to another embodiment of the invention.

FIG. 11 is a flow chart illustrating another method of using an endoscope system according to an embodiment of the invention. At 92, at least a portion of a ureter is illuminated at a first set of wavelengths. The first set of wavelengths can be, for example, a band of wavelengths associated with visible light, a band of wavelengths associated with infrared light, or a band of wavelengths associated with ultraviolet light. At 94, the portion of the ureter is illuminated at a second wavelength different than the first wavelength. The second set of wavelengths can include the same bands of wavelengths (e.g., visible light, infrared light, or ultraviolet light) as for the first set of wavelengths. At 96, a composition of a kidney stone within the ureter is identified based on the illuminating of the ureter at the first set of wavelengths and the illuminating of the ureter at the second set of wavelengths. At 98, a first image can optionally be taken of the portion of the ureter during the illuminating at the first set of wavelengths; and at 100, a second image of the portion of the ureter can be taken during the illuminating of the ureter at the second set of wavelengths. In such an embodiment, the kidney stone can be identified by comparing the first image and the second image. At 102, a medical device(s) and/or treatment parameter(s) is selected to treat the kidney stone based on the identified composition of the kidney stone. Optionally, the selected medical device can be inserted through a lumen of the endoscope at 104, and used to treat the kidney stone at 106.

Figure 12:
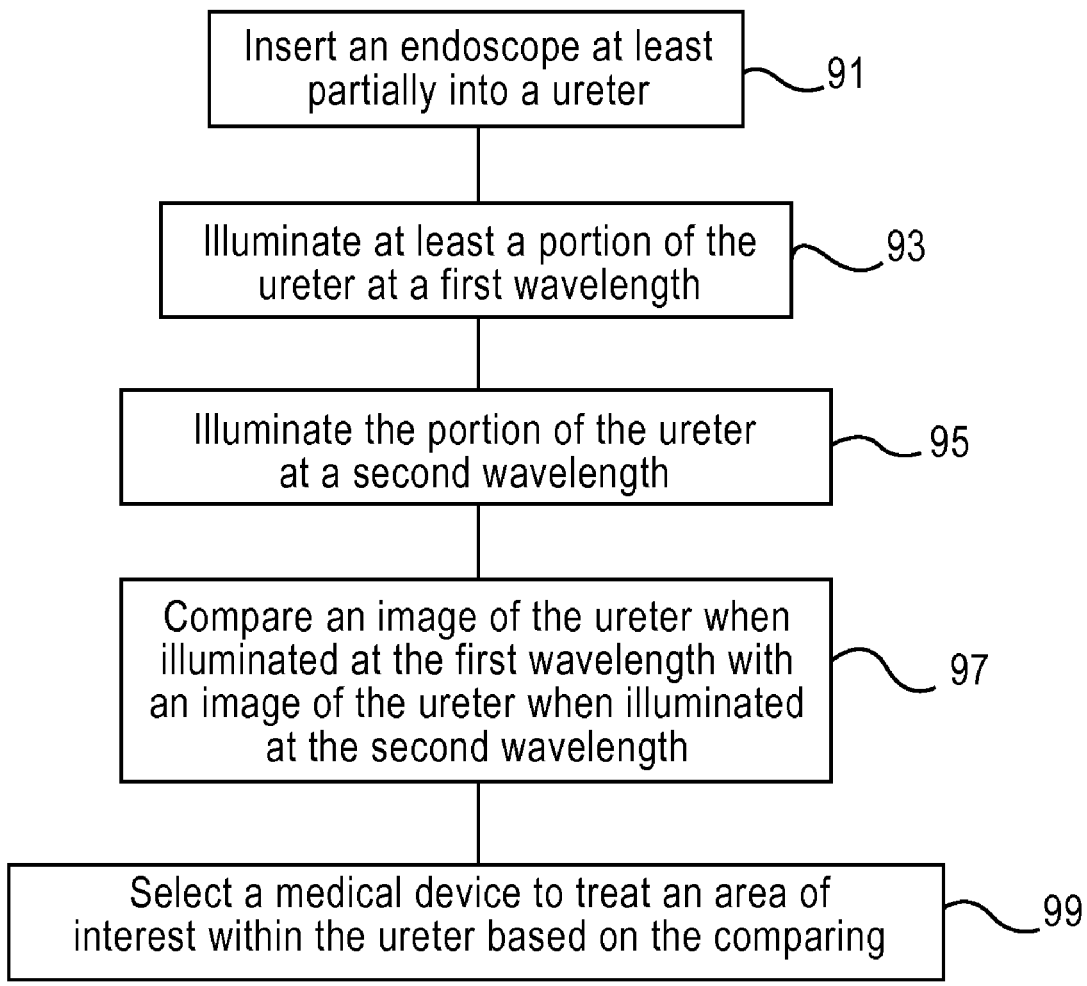
FIG. 12 is a flowchart illustrating a method according to another embodiment of the invention.

FIG. 12 is a flow chart of another method of using an endoscope system according to an embodiment of the invention. At 91, an endoscope is inserted at least partially into a ureter. At 93, at least a portion of the ureter is illuminated at a first set of wavelengths. The first set of wavelengths can be, for example, a band of wavelengths associated with visible light, a band of wavelengths associated with infrared light, or a band of wavelengths associated with ultraviolet light. At 95, the portion of the ureter is illuminated at a second set of wavelengths different than the first set of wavelengths. The second set of wavelengths can include the same bands of wavelengths (e.g., visible light, infrared light, or ultraviolet light) as for the first set of wavelengths. At 97, an image of the ureter when illuminated at the first set of wavelengths is compared to an image of the ureter when illuminated at the second set of wavelengths. At 99, a medical device(s) and/or treatment parameter(s) is selected to treat an area of interest within the ureter based on the comparing.

Some embodiments relate to a computer storage product with a computer-readable medium (also can be referred to as a processor-readable medium) having instructions or computer code thereon for performing various computer-implemented operations. The media and computer code (also can be referred to as code) may be those specially designed and constructed for the specific purpose or purposes. Examples of computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signals; and hardware devices that are specially configured to store and execute program code, such as Application-Specific Integrated Circuits (ASICs), Programmable Logic Devices (PLDs), and ROM and RAM devices. Examples of computer code include, but are not limited to, micro-code or micro-instructions, machine instructions, such as produced by a compiler, and files containing higher-level instructions that are executed by a computer using an interpreter. For example, an embodiment of the invention can be implemented using Java, C++, or other object-oriented programming language and development tools. Additional examples of computer code include, but are not limited to, control signals, encrypted code, and compressed code.

Although some embodiments herein are described in connection with optical images and the processes performed in connection with these optical images, it should be understood that all such embodiments can be considered in connection with signals (e.g., analog or digital signals) that are associated with or represent these optical images and the related processes. Similarly, to the extent that some embodiments here are described in connection with such signals, it should be understood that all such embodiments can be considered in connection with the associated optical images and the processes with respect to these optical images.

In one embodiment, a method includes inserting an endoscope at least partially into a body lumen. At least a portion of the body lumen is illuminated at a first wavelength. The portion of the body lumen is illuminated at a second wavelength different than the first wavelength. A characteristic of an area of interest when the portion of the body lumen is illuminated at the first wavelength is compared with the characteristic of the area of interest when the portion of the body lumen is illuminated at the second wavelength. A medical device(s) and/or treatment parameter(s) is selected to treat the area of interest based on the comparing.

The method can include taking a first image of the portion of the body lumen during at least a portion of the illuminating at the first wavelength and taking a second image of the portion of the body lumen during at least a portion of the illuminating at the second wavelength. The comparison of the characteristic of the area of interest can be based on the first image and the second image. In some embodiments, the comparison is performed by a processor operatively coupled to the endoscope. In some embodiments, the comparison is based on an image of the portion of the body lumen when illuminated at the first wavelength and an image of the portion of the body lumen when illuminated at the second wavelength. In some embodiments, after performing the comparison, the selected medical device can be inserted through a lumen of the endoscope and used to treat the area of interest.

In some embodiments, the illuminating at the first wavelength is substantially simultaneous with the illuminating at the second wavelength. In some embodiments, the method can also include illuminating the portion of the body lumen at a third wavelength different than the first wavelength and the second wavelength. In some embodiments, the first wavelength is a wavelength associated with visible light, and the second wavelength is a wavelength associated with infrared light. In some embodiments, the characteristic is an intensity of the area of interest. In some embodiments, the characteristic is a brightness of the area of interest. In some embodiments, the characteristic is a reflectivity of the area of interest. In some embodiments, the characteristic is a shape of the area of interest. In some embodiments, the body lumen is a ureter and the area of interest includes a kidney stone.

In another embodiment, a method includes illuminating at least a portion of a ureter at a first wavelength. The portion of the ureter is illuminated at a second wavelength different than the first wavelength. Based on the illuminating at the first wavelength and the illuminating at the second wavelength, a composition of a kidney stone is identified within the ureter. In some embodiments, the first wavelength is a wavelength associated with visible light, the second wavelength is a wavelength associated with infrared light. In some embodiments, the identifying includes comparing a characteristic of the kidney stone when the portion of the ureter is illuminated at the first wavelength and when the portion of the ureter is illuminated at the second wavelength.

In some embodiments, the method can include selecting a medical device(s) and/or treatment parameter(s) to treat the kidney stone based on the identified composition. In some embodiments, the method can include taking a first image of the portion of the ureter during the illuminating at the first wavelength and taking a second image of the portion of the ureter during the illuminating at the second wavelength. In such an embodiment, the identifying includes comparing the first image and the second image.

In some embodiments, the illuminating at the first wavelength is substantially simultaneous with the illuminating at the second wavelength and in such a case, the method can include capturing an image associated with the first wavelength and an image associated with the second wavelength of the portion of the ureter while illuminated at the first wavelength and illuminated at the second wavelength. In some embodiments, the method can include inserting an endoscope at least partially into the ureter and the endoscope is used to illuminate the ureter at the first wavelength and to illuminate the ureter at the second wavelength. In some embodiments, when an endoscope is used to illuminate the ureter at the first wavelength and illuminate the ureter at the second wavelength a processor operatively coupled to the endoscope is used to identify the composition of a kidney stone within the ureter.

In another embodiment, a method includes inserting an endoscope at least partially into a ureter. At least a portion of the ureter is illuminated at a first wavelength and illuminated at a second wavelength different than the first wavelength. An image of the ureter when illuminated at the first wavelength is compared to an image of the ureter when illuminated at the second wavelength. A medical device(s) and/or treatment parameter(s) is then selected to treat an area of interest within the ureter based on the comparing. In some embodiments, the first wavelength is a wavelength associated with visible light, the second wavelength is a wavelength associated with infrared light. In some embodiments, the area of interest is a kidney stone. In some embodiments when the area of interest is a kidney stone, the method includes determining a composition of the kidney stone based on the comparing.

In some embodiments, the method includes identifying an area of interest within the ureter before selecting a medical device and/or treatment parameter. In some embodiments, the method includes identifying a characteristic of the area of interest when illuminated at the first wavelength and identifying the characteristic of the area of interest when illuminated at the second wavelength prior to selecting a medical device and/or treatment parameter, and the comparing of the images is based on the characteristic of the area of interest. In some embodiments, the comparing includes comparing at least one of the intensity, reflectivity, brightness, or florescence of the area of interest when the portion of the ureter is illuminated at the first wavelength and the at least one of an intensity, reflectivity, brightness, or florescence of the area of interest when the portion of the ureter is illuminated at the second wavelength.

In another embodiment, a method includes illuminating at least a portion of a body lumen at a first wavelength and illuminating the portion of the body lumen at a second wavelength different than the first wavelength. The portion of the body lumen is imaged when illuminated at the first wavelength and illuminated at the second wavelength. A first image of the portion of the body lumen is produced based on the first wavelength and a second image of the portion of the body lumen is produced based on the second wavelength. In some embodiments, the method includes comparing the first image to the second image and selecting a medical device(s) and/or treatment parameters to treat an area of interest within the body lumen based on the comparing. In some embodiments, the body lumen is a ureter.

In another embodiment, a method includes inserting an endoscope at least partially into a body lumen and illuminating at least a portion of the body lumen at a wavelength. A first image is produced of the portion of the body lumen when illuminated at the wavelength. After producing the image, a fluid and/or colloid filter agent is injected into the body lumen via a lumen of the endoscope such that the filter agent at least partially contacts an area of interest within the body lumen. A second image is produced of the portion of the body lumen when illuminated at the wavelength. A characteristic of the area of interest is identified based on a comparison of the first image and the second image. In some embodiments, the method includes selecting a medical device(s) and/or treatment parameter(s) to treat the area of interest, based on the identified characteristic.

In another embodiment, a processor-readable medium storing code representing instructions to cause a processor to perform a process includes code to receive a first signal associated with a first image from an endoscope. The processor-readable medium includes code to identify a characteristic associated with an area of interest within the first image and code to receive a second signal associated with a second image from the endoscope. The processor-readable medium also includes code to identify a change in the characteristic associated with the area of interest within the second image. In some embodiments, the characteristic is at least one of color intensity, light reflectivity, brightness, or florescence, size, or shape of the area of interest. In some embodiments, the characteristic is at least one of a lithotripsy pulse rate or an energy per pulse. In some embodiments, code is included to select a medical device based on the change in the characteristic.

CONCLUSION

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents.

The previous description of the embodiments is provided to enable a person skilled in the art to make and/or use the invention. While the invention has been particularly shown and described with reference to embodiments thereof, it will be understood by those skilled in art that various changes in form and details may be made therein without departing from the spirit and scope of the invention.

For example, the endoscope systems described herein can include various combinations and/or sub-combinations of the components and/or features of the different embodiments described. Although described with reference to use within a ureter, it should be understood that the endoscopes and endoscope systems, as well as the methods of using the endoscopes and endoscope systems can be used in other body lumens.

An endoscope according to an embodiment of the invention can also be provided without the system controller described herein. For example, an endoscope can be configured to be used with other controllers, power sources, light sources, imaging devices etc., not specifically described herein. Likewise, the system controller described herein can be used with other configurations of an endoscope. An endoscope according to the invention can have a variety of different shapes and sizes, and include a different quantity of lumens than as illustrated and described herein. An endoscope according to the invention can also include other features and or components such as, for example, irrigation and suction devices and or capabilities.

What is claimed is:

1. A method, comprising:
inserting an endoscope at least partially into a body lumen;
illuminating at least a portion of the body lumen at a first wavelength;
illuminating the portion of the body lumen at a second wavelength different than the first wavelength;

comparing a characteristic of a kidney stone when the portion of the body lumen is illuminated at the first wavelength with the characteristic of the kidney stone when the portion of the body lumen is illuminated at the second wavelength;

determining a composition of the kidney stone based on the comparing; and selecting a medical device or a treatment parameter for a medical device to treat the kidney stone based on the composition of the kidney stone.

2. The method of claim 1, further comprising:

during at least a portion of the illuminating at the first wavelength, taking a first image of the portion of the body lumen; and during at least a portion of the illuminating at the second wavelength, taking a second image of the portion of the body lumen, the comparing being based on the first image and the second image.

3. The method of claim 1, further comprising:

after the comparing, inserting the selected medical device through a lumen of the endoscope; and treating the kidney stone with the selected medical device or the selected treatment parameter for the medical device.

4. The method of claim 1, wherein the body lumen is a ureter.

5. The method of claim 1, wherein the first wavelength is a wavelength associated with visible light, the second wavelength is a wavelength associated with infrared light.

6. The method of claim 1, further comprising:

illuminating the portion of the body lumen at a third wavelength different than the first wave length and the second wavelength and comparing a characteristic of the kidney stone when the portion of the body lumen is illuminated at the third wavelength with the characteristic of the kidney stone when the portion of the body lumen is illuminated at the first and second wavelengths.

7. The method of claim 1, wherein the characteristic is an intensity of the kidney stone.

8. The method of claim 1, wherein the characteristic is a brightness of the kidney stone.

9. The method of claim 1, wherein the characteristic is a reflectivity of the kidney stone.

10. The method of claim 1, wherein the characteristic is a shape of the kidney stone.

11. The method of claim 1, wherein the comparing is performed by a processor operatively coupled to the endoscope.

12. The method of claim 1, wherein the comparing is based on an image of the portion of the body lumen when illuminated at the first wavelength and an image of the portion of the body lumen when illuminated at the second wavelength.

13. The method of claim 1, wherein the illuminating at the first wavelength is substantially simultaneous with the illuminating at the second wavelength.

14. A method, comprising:

inserting an endoscope at least partially into a ureter;

illuminating at least a portion of the ureter at a first wavelength;

illuminating the portion of the ureter at a second wavelength different than the first wave length;

based on comparing a characteristic of a kidney stone at least partially within the ureter when illuminating at the first wavelength and the characteristic of the kidney stone when illuminating at the second wavelength, identifying a composition of the kidney stone within the ureter; and selecting a medical device or a treatment parameter for a medical device to treat the kidney stone based on the composition of the kidney stone.

15. The method of claim 14, further comprising:

taking a first image of the portion of the ureter during the illuminating at the first wavelength; and taking a second image of the portion of the ureter during the illuminating at the second wavelength, the identifying including comparing the first image and the second image.

16. The method of claim 14, wherein the illuminating at the first wavelength is substantially simultaneous with the illuminating at the second wavelength, the method further comprising:

capturing an image associated with the first wavelength and an image associated with the second wavelength of the portion of the ureter while illuminated at the first wavelength and illuminated at the second wavelength.

17. The method of claim 14, wherein the first wavelength is a wavelength associated with visible light, the second wavelength is a wavelength associated with infrared light.

18. The method of claim 14, wherein the illuminating at the first wavelength and the illuminating at the second wavelength is performed by the endoscope, the identifying is performed by a processor operatively coupled to the endoscope.

19. A method, comprising:

inserting an endoscope at least partially into a ureter;

illuminating at least a portion of the ureter at a first wavelength;

illuminating the portion of the ureter at a second wavelength different than the first wavelength;

comparing an image of the ureter when illuminated at the first wavelength to an image of the ureter when illuminated at the second wavelength;

determining a composition of a kidney stone within at least a portion of the ureter based on the comparing; and selecting a medical device or a treatment parameter for a medical device to treat the kidney stone within the ureter based on the composition of the kidney stone.

20. The method of claim 19, further comprising:

before the selecting, identifying the kidney stone within the ureter.

21. The method of claim 19, wherein the first wavelength is a wavelength associated with visible light, the second wavelength is a wavelength associated with infrared light.

22. The method of claim 19, further comprising:

before the selecting, identifying a characteristic of kidney stone when illuminated at the first wavelength; and identifying the characteristic of the kidney stone when illuminated at the second wavelength, the comparing being based on the characteristic of the kidney stone.

23. The method of claim 19, wherein the comparing includes comparing at least one of the intensity, reflectivity, brightness, or florescence of the kidney stone when the portion of the ureter is illuminated at the first wavelength and the at least one of an intensity, reflectivity, brightness, or florescence of the kidney stone when the portion of the ureter is illuminated at the second wavelength.

24. A method comprising:

illuminating at least a portion of a body lumen at a first wavelength;

illuminating the portion of the body lumen at a second wavelength different than the first wavelength;

imaging the portion of the body lumen when illuminated at the first wavelength and illuminated at the second wavelength;
producing a first image of the portion of the body lumen based on the first wavelength;
producing a second image of the portion of the body lumen based on the second wavelength;
comparing the first image to the second image; and
determining a composition of a kidney stone within at least a portion of the body lumen based on the comparing.

25. The method of claim 24, further comprising:
selecting a medical device or a treatment parameter for a medical device to treat the kidney stone within the body lumen based on the comparing.

26. The method of claim 25, wherein the body lumen is a ureter.

27. A method, comprising:
inserting an endoscope at least partially into a ureter;
illuminating at least a portion of the ureter at a wavelength;
producing a first image of the portion of the ureter when illuminated at the wavelength;
after the producing, injecting into the ureter via a lumen of the endoscope at least one of a fluid or colloid filter agent such that the at least one of a fluid or colloid filter agent contacts a body portion within the ureter;
after the injecting, producing a second image of the portion of the ureter when illuminated at a different wavelength;
identifying a characteristic of the body portion based on a difference between the first image and the second image;
determining a composition of a kidney stone within at least a portion of the ureter based on the difference between the first image and the second image; and
selecting a medical device or a treatment parameter to treat the body portion based on the composition of the kidney stone.

28. A processor-readable medium storing code representing instructions to cause a processor to perform a process, the code comprising code to:
receive a first signal associated with a first image from an endoscope, the image being of a kidney stone when illuminated at a first wavelength;
identify a characteristic associated with the kidney stone within the first image;
receive a second signal associated with a second image from the endoscope, the image being of the kidney stone when illuminated at a second wavelength;
identify a change in the characteristic associated with the kidney stone within the second image;
determine a composition of the kidney stone based on the change in the characteristic between the first image and the second image; and
select a medical device based on the change in the characteristic.

29. The non-transitory processor-readable medium of claim 28, wherein the characteristic is at least one of color intensity, light reflectivity, brightness, or florescence, size, or shape of the kidney stone.

30. The non-transitory processor-readable medium of claim 28, wherein the characteristic is at least one of a lithotripsy pulse rate or an energy per pulse.

* * * * *

UNITED STATES PATENT AND TRADEMARK OFFICE
CERTIFICATE OF CORRECTION

| | |
|---|---|
| PATENT NO. | : 8,280,496 B2 |
| APPLICATION NO. | : 12/332825 |
| DATED | : October 2, 2012 |
| INVENTOR(S) | : David W. Robertson |

It is certified that error appears in the above-identified patent and that said Letters Patent is hereby corrected as shown below:

Claim 28, col. 18, line 4, "a processor-readable medium" should read --A non-transitory processor-readable medium--.

Signed and Sealed this
Eighth Day of January, 2013

David J. Kappos
*Director of the United States Patent and Trademark Office*